United States Patent [19]

Veeder et al.

[11] 4,454,316

[45] Jun. 12, 1984

[54] HETEROPOLYSACCHARIDE S-139

[75] Inventors: George T. Veeder; Jerry A. Peik, both of San Diego, Calif.

[73] Assignee: Merck & Co., Inc., Rahway, N.J.

[21] Appl. No.: 339,266

[22] Filed: Jan. 15, 1982

[51] Int. Cl.³ .................... C07H 1/00; C08B 37/00; C12P 19/06; C12N 1/22

[52] U.S. Cl. .................................. 536/123; 435/101; 435/253; 536/55.1; 536/114; 536/1.1

[58] Field of Search ............... 536/1.1, 123, 114, 55.1

[56] References Cited

U.S. PATENT DOCUMENTS

| | | | |
|---|---|---|---|
| 3,960,832 | 6/1976 | Kang et al. | 536/123 |
| 4,211,774 | 7/1980 | Kang et al. | 536/123 |
| 4,304,906 | 12/1981 | Kang et al. | 536/123 |
| 4,342,866 | 8/1982 | Kang et al. | 536/123 |

*Primary Examiner*—Johnnie R. Brown
*Attorney, Agent, or Firm*—Gabriel Lopez; Hesna J. Pfeiffer

[57] ABSTRACT

The new heteropolysaccharide S-139, prepared by fermentation of an unnamed Psuedomonas species, ATCC 31644 has valuable properties as a thickening, suspending and stabilizing agent in aqueous systems.

Polysaccharide S-139 is principally composed of carbohydrate, protein (about 17%), and acyl groups (about 5% calculated as O-acetyl) as the glycosidically linked ester. The carbohydrate portion contains about 14% uronic acid (based on wt. gum) and the neutral sugars rhamnose, mannose, glucose, and galactose in the approximate molar ratio of 2.5:1:1.5:1 respectively.

3 Claims, No Drawings

HETEROPOLYSACCHARIDE S-139

BACKGROUND OF THE INVENTION

Compound S-139 may be prepared by fermentation of a suitable nutrient medium with a hitherto undescribed organism, based on extensive taxonomic studies, which is an unnamed Pseudomonas species. An unrestricted permanent deposit of a biologically pure culture of this organism, employed in making heteropolysaccharide S-139, was made with the American Type Culture Collection on May 12, 1980 under Accession No. 31644.

Various classification keys for the genus Pseudomonas and the culture description of Pseudomonas species are found in the 7th Edition of Bergey's Manual (Breed et al., (1957)) and the 8th Edition of Bergy's Manual (Doudoroff et al., (1974)), as well as by other schools in various publications; Hugh and Gilardi, 1974, *Pseudomonas, Manual of Clinical Microbiology*, 2nd ed., Lennette et al., Eds., pp. 250–269. Iizuka et al., 1963, Attempt at Grouping the Genus *Pseudomonas, J. Gen. Appl. Microbiology*, 9:73–82; and Hendric et al., 1966, Identification of Certain Species, Identification Methods for Microbiologists, Part A, Gibbs et al., Eds., pp. 1–7, Academic Press, New York.

These keys and descriptions were searched for a Pseudomonas species having morphological cultural characteristics similar to those of ATCC 31644. The following considerations make the assignment of a new Pseudomonas species justified and necessary.

DESCRIPTION OF THE STRAIN

A. Characteristics of Colonial Morphology

On nutrient agar small, yellow-pigmented, translucent colonies appear in one day at 30° C.; diameter reached 0.8–1.0 mm after 3 days' incubation. The colonies are smooth, round, entire, and drop-like. Slimy properties were not significant.

On YM agar small, opaque, yellow-pigmented, mucoid colonies appear at 30° C. in one day; diameter reached 3.0–4.2 mm after 3 days incubation. The colonies are smooth, round, entire, and drop-like. The colonies become rough after prolonged incubation. A very hard, membraneous texture is observed.

B. Characteristics of Cell Morphology

The strain S-139 is a gram-negative, rod-shaped bacterium. On nutrient agar the average size of the cell is 0.5–0.6 by 2.0–2.5 $\mu$m and tapered at both ends. Cells are often curved and vacuole-like structures appear in old cells.

On YM agar the cells are larger, average size is about 0.6–0.8 by 2.0–3.0 $\mu$m, tapered ends. Cells are often curved and elongated. Cells become more pleomorphic, elongated, and vacuolated with prolonged incubation. Motility positive; flagella stain was extremely difficult; probably multitrichously polar flagellated by Mayfield and Iniss method (1977).

C. Physiological and Biochemical Characteristics

Cytochrome oxidase, catalase positive; aerobic. Organism is capable of growth at 43° C., but not at 50° C. Survival at 60° C. for 30 minutes was observed. The organism was tolerant to 1.5%–3.0% NaCl, but not to 6.5% NaCl. Growth at pH's between 5 and 11.

Acid, but not gas, was produced from the following carbohydrates:
L-Arabinose
D-Glucose
Fructose
Galactose
Mannose
Lactose
Maltose
Melebiose
Sucrose
Trehalose
Raffinose Acid was not produced from the following carbohydrates:
Adonitol
Dulcitol
Sorbitol
Inositol
Inulin
Salicin Litmus milk was reduced. No serum zone was formed. No $H_2S$ was produced from cystine broth and TSI. ADH, LDC, and ODC were negative. Indole, VP, Simmon's citrate were negative; MR positive. Gelatin, casein, starch, egg yolk were not hydrolyzed, but Tween 80 and esculin were hydrolyzed. The 3-Ketolactose test was negative.

Organisms grow on EMB but not on MacConkey, SS agar, Mannitol salt, Pseudosel, or Tellurite Blood agars.

Congo Red dye was not observed. Tolerance to 0.02 and 0.1% triphenyltetrazolium chloride was observed.

D. Antibiotic Susceptibility Test

The strain S-139 is not susceptible to Streptomycin at 10 $\mu$g, but susceptible to the following antibiotics:

| | |
|---|---|
| Carbenicillin | 50 $\mu$g |
| Chlortetracycline | 5 $\mu$g |
| Colistin | 10 $\mu$g |
| Erythromycin | 15 $\mu$g |
| Gentamycin | 10 $\mu$g |
| Kanamycin | 30 $\mu$g |
| Neomycin | 30 $\mu$g |
| Novobiocin | 30 $\mu$g |
| Penicillin | 10 units |
| Plolymixin B | 300 units |
| Tetracycline | 30 $\mu$g |

E. Nutritional Characteristics

Growth factors are not required for growth. Ammonium salts serve as sole nitrogen source. At least 28 out of the 112 organic compounds tested are utilized as a sole source of carbon and energy. They are as follows:
D-Xylose
L-Arabinose
L-Rhamnose
D-Glucose
D-Mannose
D-Galactose
D-Fructose
Sucrose
Trehalose
Maltose
Cellobiose
Lactose
Gluconate
Salicin
Acetate
Fumarate
Succinate
Azelate
Sebacate
L-Malate Ethanol
n-Propanol
p-Hydroxybenzoate
L-α-Alanine
L-Leucine
DL-Isoleucine
L-Glutarate
L-Tyrosine F. Identification The strain S-139 is a gram-negative, aerobic, rod-shaped organism. Motile by possible multitrichous polar flagella by Mayfield and Inniss method. Oxidase and catalase are positive. Many carbohydrates are utilized. Cells have tapered ends, vacuolated form are pallisade in arrangement, and elongation is common.

According to the Bergey's Manual (8th Edition) the organism is a member of the genus Pseudomonas.

TABLE 1

Biochemical and Other Miscellaneous Tests Employed for the Strain S-139

| Oxidase: Kovac's | + | Hydrolysis of: | |
|---|---|---|---|
| Pathotech | + | Gelatin | — |
| Catalase | + | Casein | — |
| OF medium: Oxidative | + | Starch | — |
| Fermentative | — | Tween 80 | + |
| Gas from glucose | — | Pectin | — |
| $H_2S$ production: TSI | — | Alginate | NT |
| from cystine | — | Cellulose | NT |
| Ammonium from peptone | NT | Chitin | NT |
| β-Galactosidase (ONPG) | NT | DNA | NT |
| Arginine dihydrolase | — | Esculin | + |
| Lysine decarboxylase | — | Growth on | |
| Ornithine decarboxylase | — | various media: | |
| Tryptophan deaminase | NT | EMB agar | + |
| Phenylalanine deaminase | NT | MacConkey agar | + |
| Urease | NT | SS agar | — |
| Indole | — | Mannitol salt agar | — |
| MR test | + | TCB agar | — |
| VP test | — | Tinsdale tellurite | — |
| Nitrate reduction | — | blood agar | |
| Nitrate reduction | — | Pseudosel agar | — |
| Dentrification | — | | |
| $N_2$-fixation: | | Pigment production: | |
| Growth in Birk's medium | +— | King A medium | — |
| Nitrogenase activity | NT | King B medium | — |
| Malonate (Oxidation) | — | | |
| Phosphatase | — | Dye reaction: | |
| Haemolysis (sheep blood) | — | Congo red | — |
| Survival at 60° C. for 30 min | + | Nile blue | — |
| TSI: | | | |
| Slant | No change | | |
| Butt | No growth | | |
| Gas | — | | |
| Egg Yolk Reaction | — | | |
| Litmus milk: | | | |
| change in color | — | | |
| peptonization | — | | |
| reduction | + | | |

— = negative
+ = positive
NT = not tested

FERMENTATION CONDITIONS

Heteropolysaccharide S-139 is produced during the aerobic fermentation of suitable aqueous nutrient media under controlled conditions via the inoculation with the organism of the unnamed Pseudomonas species. The media contain sources of assimilable carbon, nitrogen, and inorganic salts.

In general, carbohydrates (for example, glucose, fructose, maltose, sucrose, xylose, mannitol and the like) can be used either alone or in combination as sources of assimilable carbon in the nutrient medium. The exact quantity of the carbohydrate source or sources utilized in the medium depend in part upon the other ingredients of the medium but, in general, the amount of carbohydrate usually varies between aout 2% and 4% by weight of the medium. These carbon sources can be used individually, or several such carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn steep liquor, distiller's solubles or tomato paste and the like. The sources of nitrogen, either alone or in combination, are used in amounts ranging from about 0.05% to 0.2% by weight of the aqueous medium.

Among the nutrient inorganic salts which can be incorporated in the culture media are the customary salts capable of yielding sodium, potassium, ammonium, calcium, phosphate, sulfate, chloride, carbonate, and the like ions. Also included are trace metals such as iron and magnesium.

It should be noted that the media described in the examples are merely illustrative of the wide variety of media which may be employed, and are not intended to be limitative.

As an alternate medium, S-139 may be grown under low $Ca^{++}$ conditions, i.e., in deionized water or some other aqueous system substantially free of $Ca^{++}$ ions (i.e., less than about 4 ppm $Ca^{++}$ per 1% gum in the final fermentor broth).

The fermentation is carried out at temperatures ranging from about 25° C. to 35° C.; however, for optimum results it is preferable to conduct the fermentation at temperatures of from about 28° C. to 32° C. The pH of the nutrient media for growing the Pseudomonas culture and producing the polysaccharide S-139 can vary from about 6 to 8.

Although the polysacaride S-139 is produced by both surface and submerged culture, it is preferred to carry out the fermentation in the submerged state.

A small scale fermentation is conveniently carried out by inoculating a suitable nutrient medium with the culture, and after transfer to a production medium permitting the fermentation to proceed at a constant temperature of about 30° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 30° C. for 1–2 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are recovered by precipitation with a suitable alcohol such as isopropanol.

For large scale work, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 30° C. This method of producing the S-139 is particularly suited for the preparation of large quantities.

The product is recovered from the fermentation medium by precipitation with a suitable alcohol, such as isopropanol.

HETEROPOLYSACCHARIDE S-139

The heteropolysacharide produced by the unnamed Pseudomonas species, ATCC 31644, is composed principally of carbohydrate with 5.0% O-acyl groups as the O-glycosidically linked ester.

The carbohydrate portion of the S-139 polysaccharide contains 14–15% (based on weight gum) galacturonic acid and the neutral sugars galactose, mannose, glucose and rhamnose. The approximate molar ratios of these neutral sugars are: rhamnose, 2.5; glucose, 1.5; mannose, 1.0; and galactose, 1.0.

The acetyl content of 5.0% was determined by treating a 0.2% aqueous solution of S-139 gum with an alkaline, hydroxylamine reagent followed by treatment with an acidic ferric chloride reagent [S. Hestrin (1949) *J. Biol. Chem.* 180 249-2611].

The neutral sugars of polysaccharide S-139 were determined by dissolving ten mg. of the product in 2 ml 2N $H_2SO_4$, and the mixture is heated at 100° C. for 4 hours. The resulting solution is cooled, neutralized with barium hydroxide and the pH is brought to 5–6 with solid carbon dioxide. The resulting precipitate of barium sulfate is removed by centrifugation and the supernatent is concentrated to a syrup under reduced pressure. The sugars in the hydrolysate are tentatively identified by gas-liquid chromatography of their aldononitrile acetate derivatives on a Hewlett-Packard Model 5750 chromatograph using 3% by weight OV-225 on 80/100 mesh Gas Chrome Q at 210° C. The sugars are identifed and quantitated by comparison with authentic standards [J. K. Baird, M. J. Holroyde, and D. C. Ellwood (1973) *Carbohydr. Res.* 27 464–467].

The uronic acid content of the polysaccharide was determined by two separate methods. In one method the sample was decarboxylated with 19% hydrochloric acid and the liberated carbon dioxide was trapped in standard sodium hydroxide and determined by back titration [B. D. Browning (1967) *Method of Wood Chemistry*, II, 632–633] and by the carbazole colorimetric method [T. Bitter and H. M. Muir (1962) *Anal. Biochem.*, 4 330–334].

Paper electrophoresis was used for the separation and tentative identification of the uronic acids present in the neutralized acid hydrolysate described above. Aliquots of this and known uronic acid standards were applied to Camag electrophoresis paper No. 68-011 and electrophoresis was carried out for 2.0 hours in a pH 2.7 buffer using a Camag Model HVE electrophoresis apparatus. Chromatograms were air dried and stained with silver nitrate dip reagent to locate the uronic acids being separated. One major uronic acid spot was found. The major spot migrated with the same mobility as galacturonic acid.

The polysaccharide S-139 has been found to have the following outstanding properties: high viscosity (1% vis. in STW=1890 cP); a high working yield value (95 dynes/$cm^2$, 1% in STW); good salt compatibility; excellent stability at elevated temperatures; excellent pH and enzyme stability. Therefore, S-139 biogum has utility in various industrial (e.g., petroleum) and food applications where high viscosity, high yield point, excellent thermal, salt, pH, and enzyme stability are desirable. It is useful as a thickening, suspending, emulsifying, stabilizing, lubricating, film-forming, or binding agent, especially in aqueous systems. In particular, it has uses in the following applications or products: adhesives, wall-joint cements, water-retentive grouts and mortars, spackling compounds, can sealing, boiler compounds, latex creaming, welding-rod fluxes, brazing pastes, ceramic glazes and extrusions, cleaners and polishes, toys, emulsions (latex, asphalt, silicone), silver recovery, seed coatings, spray control for pesticides or herbicides, emulsifiable concentrates and flowable pesticides and herbicides, tobacco binders, water-based inks, lithographic fountain solutions, leather finishes, hydromulching and hydro-seeding, textile printing and finishing, wet-end paper additives, wet-end paper retention and formation aid, anti-stick compounds, mold-release agents, liquid resins, slurry and packaged explosives, petroleum and water-well drilling muds, petroleum workover and completion fluids, petroleum stimulation fluids, cosmetics, pharmaceutical suspensions and emulsions.

Also this gum has utility in food systems such as jellies and other high sugar systems, beverages including citric acid based drinks, dairy products including ice cream and yogurt, salad dressing, dry mixes, icings, and glazes, syrups, puddings, farinaceous foods, canned and retorted foods, and bakery fillings.

A use for S-139 is in the field of petroleum and water-well drilling muds. A typical formulation for a fresh-water mud is as follows:

| S-139 | | | 1.0 lbs | | |
|---|---|---|---|---|---|
| Bentonite | | | 10.0 lbs | | |
| Fresh Water | | | 1.0 bbl | | |
| Fann Viscosity Data: | | | | | |
| Speed (rpm) | 3 | 6 | 100 | 200 | 300 | 600 |
| Dial Reading | 11 | 12 | 22 | 29 | 34 | 52 | pH = 8.5
API Filtrate = 10.0

Another formula, for a salt-water mud, is:

| S-139 | | | 1.0 lb | | |
|---|---|---|---|---|---|
| Sea Water | | | 1.0 bbl | | |
| Fann Viscosity Data: | | | | | |
| Speed (rpm) | 3 | 6 | 100 | 200 | 300 | 600 |
| Dial Reading | 2.0 | 2.4 | 6.4 | 9.0 | 11 | 18 | pH = 7.9
API Filtrate = 18.0

Although S-139 gum possesses a general viscosity-imparting property, its particular profile of solution properties is a distinctive characteristic which enables it to be distinguished from other heteropolysaccharides.

In its dry form, (through 60 mesh), it is an ecru colored powder with a moisture content of about 6.40% and an ash content of about 9.20% (solids basis). Its most useful mesh size is 100% through 40 mesh, with no more than 30% through 325 mesh. The gum has the following profile of properties:

1. VISCOSITY AND SHEAR
A. Brookfield LVT

| | Viscosity (cP) Syn. Tap Water (Spin. No. 3) |
|---|---|
| 1. 1.0% at 60 rpm | 1890 |
| at 6 rpm | |
| 2. 0.5% at 60 rpm | 600 |
| 3. 0.1% at 60 rpm | 35 |

B. Brookfield LVT with UL Adaptor

| Conc. % | RPM | Visc. (cP) |
|---|---|---|
| 0.10 | 60 | >10.0 |
| | 6 | 49.5 |
| 0.05 | 60 | 5.7 |
| | 6 | 17 |
| 0.01 | 60 | 1.7 |
| | 6 | 2.0 |

C. Wells Micro Brookfield

| | Working Yield Value (dynes/cm$^2$) |
|---|---|
| 1% in STW | 95.0 |

D. Shear Stability

| Conc. | Time Sheared (min.) | Temp. | Brookfield (LVT) Visc. at R.T., 60 rpm (cP) | % Visc. Change |
|---|---|---|---|---|
| | 0 | 24.5° C. | 1170 | |
| 0.75% in STW | 15 | 55° C. | 1550 | +32.5 |

Blender setting 7
Variac highest setting at 120 volt

2. STORAGE
A. 4.4° C. Storage
3000 cP at 60 rpm with spindle β4; gum is gel-like; not a moldable gel.

B. Elevated Temperature Storage Stability
1. Dry Powder - 50° C. (120° F.)

| Days | Brookfield (LVT) Viscosity (cP) α 60 rpm, 1% in STW | % Vis. Change |
|---|---|---|
| 0 | 2340 | |
| 1 wk. | 1900 | −18.8 |
| 2 wks. | 1970 | −15.8 |
| 4 wks. | 1970 | −15.8 |

2. 1% Solution in STW - 70° C. (158° F.)

| Days | Brookfield (LVT) Viscosity at R.T. 60 rpm, cP | % Vis. Change |
|---|---|---|
| 0 | 2340 | |
| 2 | 2850 | +22 |
| 7 | 2200 | −6 |

3. ACID, BASE, HEAT STABILITY

| Stability | Initial n | Final n | % Change |
|---|---|---|---|
| 1. Acetic acid plus heat (96° C., 5 min) | 2950 cP | Gel | Gel |
| 2. 1% HCl plus heat (2 hrs. at 80° C.) | Ppt | Ppt | — |
| 3. 1% NaOH plus heat (2 hrs at 80° C.) | 1540 cP | 30 cP | −98 |

4. Heat vs. Visc (1% conc.) in STW

| Temp. (°C.) | Visc. (cP) |
|---|---|
| 26.7 | 41.4 |
| 32.2 | 41.2 |
| 37.8 | 40.0 |
| 48.9 | 38.0 |
| 60.0 | 36.6 |
| 71.1 | 35.2 |
| 82.2 | 34.4 |
| 93.3 | 34.0 |
| 104.4 | 34.0 |
| 121.1 at 0 min. | 33.6 |
| 121.1 at 15 min | 32.0 |
| 26.7 | 48.8 (118% visc. recovery) |

5. Viscosity vs. pH

| pH | Brookfield (LVT) Viscosity, cP 1% in STW |
|---|---|
| 1.8 | 410 |
| 2.35 | 2650 |
| 3.1 | 2550 |
| 4.9 | 1910 |
| 7.0 | 1910 |
| 8.15 | 1830 |
| 8.95 | 1820 |
| 11.2 | 1810 |
| 12.1 | 2200 |
| 12.1 | 830 |

Initial pH and Viscosity

6. pH Effect (Wells-Brookfield Microviscomete Model RVT-c/P at 9.6 sec$^{-1}$)

| 1. 5% Acetic acid | 2.88 pH | 1790 cP |
|---|---|---|
| 2. 5% NH$_4$OH | 10.70 pH | >2560 cP |

4. SALT AND DYE COMPATIBILITY
A. Salt

| 1. CaCl$_1$ (Saturated) | Compatible |
|---|---|
| 2. Amm. polyphosphate | Precipitate |
| 3. 60% NH$_4$NO$_3$ | Precipitate |
| 4. 1% Al$_2$(SO$_4$)$_3$ 18H$_2$O | Compatible |
| 5. 1% CaCl$_2$.2H$_2$O | Compatible |
| 6. 1% KCl | Compatible |
| 7. 0.1% KCl | 2230 cP |
| 8. 2.5% KCl | 1610 cP |

B Solubility in Salt Containing Systems

| | Fann Model 35, Viscosity, cP | | |
|---|---|---|---|
| | 600 rpm | 300 rpm | 200 rpm |
| Sea Water | 7.75 | 10.3 | 12.45 |
| Sat. CaCl$_2$ 2H$_2$O | 9.65 | 9.8 | 10.05 |
| Permian Brine | 12.8 | 9.9 | 11.1 |
| Standard Brine | 11.2 | 16.5 | 21.15 |

| | Fann Model 35, Viscosity, cP | | |
|---|---|---|---|
| | 100 rpm | 6 rpm | 3 rpm |
| *Sea Water | 18 | 125 | 220 gel like |
| Sat. CaCl$_2$.2H$_2$O | 10.5 | 35 | 50 |
| **Permian Brine | 13.8 | 65 | 110 |
| *Standard Brine | 33 | 290 | 520 |

*Partially souble
**Soluble

C. Dyes

| 1. Milling Green | Compatible |
|---|---|
| 2. Methylene Blue | Precipitate |

5. TEXTURE/FLOW PROPERTIES

Very chunky flow, not continuous; high viscosity; light pink in coloration; very gummy to the touch.

6. MILK REACTIVITY

| A. Dispersion | Poor, grainy |
|---|---|
| B. Whey off | 1st day |

7. FILM FORMATION

Uneven pull down; film formed; plastic, high tensile strength.

EXAMPLE 1

Fermentation Procedure for Producing Heteropolysaccharide S-139

A. Culture Maintenance

The unnamed Pseudomonas organism, ATCC 31644, grows quite well on nutrient agar at an incubation temperature of 30° C. This organism produces a yellow carotenoid pigment. The colonies on NA are small (only 1-2 mm) after such incubation for three days. Colonies are round, smooth, concave, opaque and yellow pigmented.

B. Seed Preparation

Flask seeds are prepared in YM broth and incubated with shaking at 30° C. for this medium. The culture will typically give viscous growth by 24-30 hrs. The YM seeds are then used to inoculate seed medium, which is the same as final fermentor medium, except that the phosphate concentration is increased to 0.5%. One gallon fermentors are used as seed vessels for the 20L and 70L fermentors.

C. Final Fermentor Medium

The following medium gives acceptable results in both 20L and 70L fermentors.

|  |  |
|---|---|
| Glucose | 3.0% |
| $K_2HPO_4$ | 0.05% |
| Promosoy 100[1] | 0.05% |
| $NH_4NO_3$ | 0.09% |
| $MgSO_4\ 7H_2O$ | 0.01% |
| $Fe^{++}$ | 1 ppm |

1. An enzymatic digest of soybean meal.

An agitation rate of 300 rpm in both the 20L and 70L fermentors is desirable at the start of the fermentation. The agitation is then increased as the viscosity increases to provide adequate mixing. An air flow rate of 10L/min (20L) or 20L/min (70L) is desirable and is maintained throughout the fermentation. Fermentation times range from 60-90 hrs with beer viscosities ranging from 3000-7000 cps. Conversion efficiency varies from 40-55% with 3% glucose. Small amounts of commercially available antifoam agent can be used. The pH is controlled at 6.7 or greater by the addition of KOH using automatic pH control equipment.

D. Recovery

Fermentation beer is pasteurized at 167° F. for 10-15 min. Due to the excellent heat stability exhibited by this product, higher pasteurization temperatures with shorter holding times should be aceptable. Good fibers are typically produced under precipitation conditions using 2 volumes of IPA per volume of beer.

E. Drying

All product recovered thus far has been dried at 50°-55° C. for up to one hour in a forced air tray drier.

The properties of S-139 gum produced during these fermentation conditions have been given above.

What is claimed is:

1. Heteropolysaccharide S-139, which comprises principally carbohydrate, about 17% protein and about 5% (calculated as O-acetyl) acyl groups as the glycosidically linked ester, the carbohydrate portion containing about 14% galacturonic acid (based on the wt. of gum) and the neutral sugars rhamnose, mannose, glucose and galactose in the approximate molar ratio of 2.5:1:1.5:1.

2. The heteropolysaccharide of claim 1 prepared by a process which comprises growing the organism ATCC 31644 in an aqueous nutrient medium by submerged, aerobic fermentation of an assimilable carbon source and recovering said heteropolysacharide.

3. The heteropolysaccharide of claim 2, wherein the nutrient medium is substantially free of $Ca^{++}$ ions.

* * * * *